(12) United States Patent
Duck

(10) Patent No.: US 9,193,819 B2
(45) Date of Patent: Nov. 24, 2015

(54) POLYMERS, SUBSTRATES, METHODS FOR MAKING SUCH, AND DEVICES COMPRISING THE SAME

(71) Applicant: Avertica, Inc., Research Triangle Park, NC (US)

(72) Inventor: Nicholas Brendan Duck, Chapel Hill, NC (US)

(73) Assignee: Avertica, Inc., Research Triangle Park, NC (US)

( * ) Notice: Subject to any disclaimer, the term of this patent is extended or adjusted under 35 U.S.C. 154(b) by 0 days.

(21) Appl. No.: 14/173,269

(22) Filed: Feb. 5, 2014

(65) Prior Publication Data

US 2014/0220457 A1    Aug. 7, 2014

Related U.S. Application Data

(60) Provisional application No. 61/761,499, filed on Feb. 6, 2013.

(51) Int. Cl.

| | | |
|---|---|---|
| *C08G 12/04* | (2006.01) | |
| *C08J 3/24* | (2006.01) | |
| *C08G 12/08* | (2006.01) | |
| *C08G 12/40* | (2006.01) | |
| *H01G 9/004* | (2006.01) | |
| *C08G 67/00* | (2006.01) | |
| *C08L 61/22* | (2006.01) | |
| *C08L 61/32* | (2006.01) | |
| *H01G 11/48* | (2013.01) | |
| *H01G 9/00* | (2006.01) | |
| *H01M 4/62* | (2006.01) | |
| *H01G 11/26* | (2013.01) | |

(52) U.S. Cl.
CPC ............... *C08G 12/04* (2013.01); *C08G 12/08* (2013.01); *C08G 12/40* (2013.01); *C08G 67/00* (2013.01); *C08J 3/24* (2013.01); *C08L 61/22* (2013.01); *C08L 61/32* (2013.01); *H01G 9/004* (2013.01); *C08J 2361/32* (2013.01); *H01G 11/26* (2013.01); *H01G 11/48* (2013.01); *H01G 2009/0007* (2013.01); *H01M 4/622* (2013.01); *Y02E 10/549* (2013.01); *Y02E 60/122* (2013.01); *Y02E 60/13* (2013.01); *Y02E 60/50* (2013.01)

(58) Field of Classification Search
None
See application file for complete search history.

(56) References Cited

U.S. PATENT DOCUMENTS

| | | |
|---|---|---|
| 5,015,699 A | 5/1991 | Cotts et al. |
| 5,070,183 A | 12/1991 | Kim |
| 5,098,836 A | 3/1992 | Stahl et al. |
| 6,025,462 A | 2/2000 | Wang et al. |
| 7,034,164 B1 | 4/2006 | Cosnier |
| 7,964,673 B2 | 6/2011 | Shiba et al. |
| 8,138,163 B2 | 3/2012 | Chung et al. |
| 2007/0042266 A1 | 2/2007 | Oh et al. |

FOREIGN PATENT DOCUMENTS

| | | |
|---|---|---|
| JP | 01-118515 | 5/1989 |
| JP | 10-262690 | 10/1998 |
| JP | 10-262690 A | 10/1998 |
| RU | 2075482 C1 | 3/1997 |
| RU | 2446213 C2 | 3/2012 |
| WO | WO 86/01902 | 3/1986 |

OTHER PUBLICATIONS

CIANGA. European Polymer Journal, 2006, 42, 1922-33.*

Amari et al., "Thiophene containing Schiff bases oligomers and polymers. Synthesis, characterization and properties" *Synthetic Metals* 1995, 72:7-12.

Amari et al., "Optical waveguide fabrication using a polymeric azine containing the 3-dodecyltheiopehen moiety" *Journal of Materials Chemistry* 1996, 6(8):1319-1324.

Ardaraviciene et al., "Symmetrical azine-based pliymers possessing 1-phenyl-1,2,3,4-tertrahydroquinoline moieties as materials for optoelectronics" *Reactive & Functional Polymers* 2011, 71:1016-1022.

Bethell et al., "Oligomeric bis(1,3-indandiylidene)azines: preparation, electrochemical and spectroscopic properties, and implications for the use of polyazines as conducting materials" *Journal of the Chemical Society, Perkin Transactions* 2 1996, 1081-1086.

Bolduc et al., "EDOT-containing azomethine: an easily prepared electrochromatically active material with tuneable colours" *The Royal Chemical Society—Journal of Materials Chemistry* 2010, 20:4820-4826.

Bolto et al., "Electronic Conduction in Polymers" *Australian Journal of Chemistry* 1963, 16:1090-1103.

Cao et al., "A New Dopable Soluable Electrically Conducting Polyazine Polymer" *Journal of the Chemical Society, Chemical Communications* 1988, 937-938.

Chaloner-Gill et al., "Structure of Glyoxal Dihydrazone and Synthesis, Characterization, and Iodine Doping of Unsubstituted Polyazine" *Macromolecules* 1990, 23:4597-4603.

Chaloner-Gill et al., "$^{13}$C and $^{15}$N Solid-State NMR of Partially Methyl Substituted Polyazines" *Macromolecules* 1991, 24:3074-3080.

Choytun et al., "Azines possessing strong push-pul donors/acceptors" *The Royal Chemical Society—Chemical Communications* 2004, 1842-1843.

(Continued)

*Primary Examiner* — Noble Jarrell
(74) *Attorney, Agent, or Firm* — Myers Bigel Sibley & Sajovec, P.A.

(57) ABSTRACT

The present invention relates generally to substrates for making polymers and methods for making polymers. The present invention also relates generally to polymers and devices comprising the same.

15 Claims, 10 Drawing Sheets

(56) References Cited

OTHER PUBLICATIONS

Cotts et al., "Equilibrium Flexibility of a Rigid Linear Conjugated Polymer" *Macromolecules* 1996, 29:7323-7328.
Destri et al., "Synthesis and Characterization of Conjugated Polyazines and Polyazomethines Containing the Thienylene Moiety and Flexible Hydrocarbon Side Charms" *Macromolecules* 1999, 32:353-360.
Dudis et al., "Iodine-Doped Polyazines: Evidence against Bipolarons and Nitrenium Ions[1]" *Journal of the American Chemical Society* 1993, 115:8770-8774.
Dufresne et al., "Towards materials with reversible oxidation and tuneable colours using heterocyclic conjugated azomethines" *Journal of Materials Chemistry* 2010, 20:4861-4866.
Euler, "IR Spectroscopy of Pristine and Iodine-Doped Permethylpolyazine" *Chemistry of Materials* 1996, 8:554-557.
Euler, "Synthesis, characterization, and iodine doping of a soluble polyazine: the propyl-methyl substituted derivative" Chemistry of Materials 1990, 2(2):209-213.
Evans et al,, "Polymers Based on Hydrazine. Part I" *Journal of the Chemical Society* 1963, 3523-3528.
Geim, "Graphene: Status and Prospects" *Science* 2009, 324:1530-1534.
Getautis et al., "Novel hydrazone based polymers as hole transporting materials" *Polymer* 2005, 46:7918-7922.
Getautis et al., "Novel hydrazone moieties containing polymers for optoelectronics" *Journal of Photochemistry and Photobiology A: Chemistry* 2006, 180:23-27.
Getautis et al., "Novel dihydrazone based polymers for electrophotography" *European Polymer Journal* 2007, 43:3597-3603.
Hauer et al., "Structure of 2,3-butanedione dihydrazone and IR study of higher polyazines: a new class of polymeric conductors" *Journal of the American Chemical Society* 1987, 109:5760-5765.
Hong et al, "A conjugated polyazine containing diketopyrrolopyrrole for ambipolar organic thin film transistors" *The Royal Chemical Society—Chemical Communications* 2012, 48:8413-8415.
Inoue, "Functional dendrimers, hyperbranched and star polymers" *Progress in Polymer Science* 2000, 25:453-571.
Iwan et al., "Liquid-crystalline phases formed by symmetrical azines with different terminal chains: Thermal, optical and electrical study" *Synthetic Materials* 2010, 160:859-862.
Kesslen et al., "Synthesis and Characterization of Pyridine End-Capped Oligoazines" *Tetrahedron Letters* 1995, 36(27):4725-4728.
Kumar et al., "Advances in Conductive Polymers" *European Polymer Journal* 1998, 34(8): 1053-1060.
Lewis et al., "Near-perfect dipole parallel-alignment in the highly anistropic crystal structure of 4-iodoacetophenone-(4-methoxyphenylethylidene) hydrazone[(1)]" *Journal of Chemical Crystallography* 2000, 30(7):489-496.
Makowski, "Mesoporous Poly(benzimidazole) as a Purely Organic Heterogeneous Catalyst for the Knoevenagel Condensation" *Catalysis Communication* 2008, 10(2):243-247.
Moreno-Mañas et al., "The first 1,3-dithiol-2-ylindene donor-π-acceptor chromophores containing an azine space: synthesis, electrochemical and nonlinear optical properties" *Journal of Materials Chemistry* 2001, 11:374-380.
Mostert et al., "Role of semi conductivity and ion transport in the electrical conduction of melanin" *Proceedings of the National Academy of Sciences* 2012, 109(23):8943-8947.

Mukherjee et al., "Soluable and processable conjugated polyazines with oligo(p-phenylene vinylene)s" *Tetrahedron Letters* 2008, 49:1037-1040.
Ng et al., "Novel electrically conductive polyheteroarylene azines" *Journal of Material Science Letters* 1997, 16:841-842.
Pohl, "The Nature and Properties of Giant-Orbital Polymers" *Journal of Polymer Science: Part A: Polymer Chemistry Edition* 1986, 24:3057-3075.
Price et al., "Fluorine Substituted Conjugated Polymer of Medium Band Gap Yields 7% Efficiency in Polymer-Fullerene Solar Cells" *Journal of the American Chemical Society* 2011,133(12):4625-4631.
Saxena et al., "Structural and thermal characterization of metal halides doped polypyrrole" *Indian Journal of Pure & Applied Physics* 2008, 46:414-416.
Schmidt et al., "Microporous Conjugated Poly(thienylene arylene) Networks" *Advanced Materials* 2009, 21:702-705.
Sek et al., "Synthesis and study on the light absorbing, emitting, redox and electrochromic properties of azines and polyazines with thiophene units" *Synthetic Metals* 2012, 162:1623-1635.
Shirakawa et al., "Synthesis of Electrically Conducting Organic Polymers: Halogen Derivatives of Polyacetylene, $(CH)_x$," *Journal of the Chemical Society, Chemical Communications* 1977, 578-580.
Tindale et al., "Electrochemistry and photoelectrochemistry of two donor-acceptor polythiophene polymers with acceptor moieties in the main chain" *Journal of Electroanalytical Chemistry* 2008, 612:219-230.
Weder, "Synthesis, processing and properties of conjugated polymer networks" *The Royal Society of Chemistry—Chemical Communications* 2005, 5378-5389.
Yang et al., "Conjugated Aromatic Polyimines. 2. Synthesis, Structure, and Properties of New Aromatic Polyazomethines" *Macromolecules* 1995, 28:1180-1196.
Zhang et al., "Chemical synthesis of PEDOT nanofibers" *Chemical Communications* 2005, 42:5328-5330.
Zimmerman, "Polyazines. I. The Structure of the Dimethyl Aziethane of Curtius and Thun[1]" *Journal of the American Chemical Society* 1936, 58:948-949.
International Search Report and the Written Opinion of the International Searching Authority Corresponding to International Application No. PCT/US2014/015081; Date of Mailing: Jul. 10, 2014 (7 pages).
International Search Report and the Written Opinion of the International Searching Authority Corresponding to International Application No. PCT/US2014/015094; Date of Mailing: May 7, 2014 (9 pages).
International Search Report and the Written Opinion of the International Searching Authority corresponding to International Application No. PCT/US2014/015081:7 pages (mailed Jul. 10, 2014).
International Preliminary Report on Patentability corresponding to International Patent Application No. PCT/US2014/015081 (6 pages) (dated Aug. 11, 2015).
International Preliminary Report on Patentability corresponding to International Patent Application No. PCT/US2014/015094 (7 pages) (dated Aug. 11, 2015).
International Search Report and the Written Opinion of the International Searching Authority corresponding to International Patent Application No. PCT/US2014/015081 (7 pages) (mailed Jul. 10, 2014).

* cited by examiner

US 9,193,819 B2

POLYMERS, SUBSTRATES, METHODS FOR MAKING SUCH, AND DEVICES COMPRISING THE SAME

RELATED APPLICATIONS

This application claims the benefit of and priority to U.S. Provisional Application Ser. No. 61/761,499, filed Feb. 6, 2013, the disclosure of which is hereby incorporated by reference herein in its entirety.

FIELD OF THE INVENTION

The present invention relates generally to substrates for making polymers and methods for making polymers. The present invention also relates generally to polymers and devices comprising the same.

BACKGROUND OF THE INVENTION

Conjugated polymeric systems have been an area of research as some can provide conductive and light emitting and absorbing properties and thus have utility in electronics, molecular electronics and optoeletronics. Conjugated polymers have been made from various monomers and by various methods to yield a variety of polymers each with unique physical and electrical properties. These polymers include poly acetylenes, poly(pyrrole)s, polyanilines, polyazines, poly(p-phenylene vinylene), polycarbazoles, polyindoles, polyazepines poly(thiophene)s, poly(3,4-ethylenedioxythiophene), poly(p-phenylene sulfide), poly(fluorene)s, polyphenylenes, polypyrenes, polyazulenes, polynaphthalenes and polybenzimidazoles. These are generally linear polymers with variable chain lengths that are described in the literature.

Polyarylenes are a group of aromatic conjugated polymers that are branched and dendritic. Polyarylenes are made by the reaction of alkynes or with aromatic halides in the presence of metal catalysts. These are generally granular, globular or have a coil morphology. Variations of these polymers include polymers made with branched side chains or dendritic structures and polymers with branched monomers incorporated with more than one site for polymer extension. These later polymers result in branched polymers, where the conjugated backbone bifurcates. Each has unique electronic, optical and magnetic properties. However, because all of these reactions are unidirectional, all of the polymers eventually terminate, forming powders or microspheres and do not form a networked solid material.

The present invention addresses previous shortcomings in the art by providing substrates for making conjugated polymers and methods for making conjugated polymers.

SUMMARY OF THE INVENTION

Embodiments according to the invention are directed to substrates, polymers, methods, and devices. In some embodiments, a substrate of the present invention may be used to prepare a polymer of the present invention. Thus, in some embodiments provided is a substrate as described herein. Pursuant to these embodiments, provided herein is a polymer as described herein.

Also provided herein are methods for preparing a polymer of the present invention. One aspect of the present invention comprises a method of preparing an organic polymer, comprising polymerizing a multifunctional synthetic organic substrate with an oxidase to form said organic polymer.

An additional aspect of the present invention comprises a method of preparing an organic polymer, comprising polymerizing a multifunctional organic substrate with an oxidizing agent to form said organic polymer.

A further aspect of the present invention comprises a method of preparing a cross-linked polyazine polymer, comprising reacting an organic substrate comprising at least two aldehydes and/or ketones with a multiamine to form an organic polymer; and oxidizing said organic polymer to form said cross-linked polyazine polymer.

In a further aspect of the present invention, provided is a device, such as, but not limited to, an electrochemical device, comprising a polymer of the present invention.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

Figure 1:
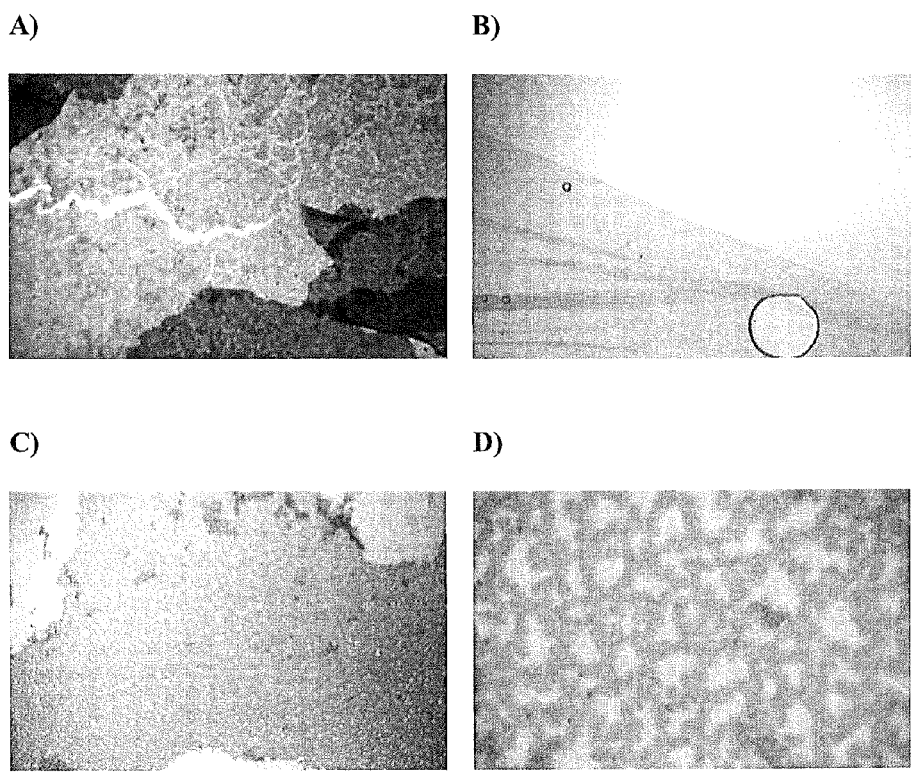
FIGS. 1A-D show polymer sheet networks prepared using compound 2 and either 5-hydroxyindole, serotonin, or indole. A) Compound 2 and 5-hydroxyindole networked polymer at 200× magnification. B) Compound 2 and serotonin networked polymer at 200× magnification. C) Compound 2 and indole networked polymer at 200× magnification. D) Compound 2 and indole networked polymer at 400× magnification.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety for the teachings relevant to the sentence and/or paragraph in which the reference is presented. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value such as an amount or concentration and the like, is meant to encompass variations off 20%, ±10%, ±5%, ±1%, ±0.5%, or even ±0.1% of the specified amount. A range provided herein for a measureable value may include any other range and/or individual value therein.

It will be understood that when an element or layer is referred to as being "on," "connected to," or "coupled with" another element or layer, it can be directly on, connected, or coupled with the other element or layer or intervening elements or layers may be present. In contrast, when an element is referred to as being "directly on," "directly connected to," or "directly coupled with" another element or layer, there are no intervening elements or layers present.

"Moiety" or "moieties," as used herein, refer to a portion of a molecule, such as a portion of a substrate, typically having a particular functional or structural feature. For example, a moiety may comprise a linking group (a portion of a molecule connecting at least two other portions of the molecule). In some embodiments, a moiety may be a reactive portion of a substrate.

"Substituted" as used herein to describe a chemical structure, group, or moiety, refers to the structure, group, or moiety comprising one or more substituents. As used herein, in cases in which a first group is "substituted with" a second group, the second group is attached to the first group whereby a moiety of the first group (typically a hydrogen) is replaced by the second group. The substituted group may contain one or more substituents that may be the same or different.

"Substituent" as used herein references a group that replaces another group in a chemical structure. Typical substituents include nonhydrogen atoms (e.g., halogens), functional groups (such as, but not limited to, amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include, but are not limited to, alkyl, lower alkyl, halo, haloalkyl, alkenyl, alkynyl, cycloalkyl, cycloalkylalkyl, heterocyclo, heterocycloalkyl, aryl, arylalkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silylalkyl, silyloxy, boronyl, and modified lower alkyl.

"Alkyl" as used herein alone or as part of another group, refers to a linear ("straight chain"), branched chain, and/or cyclic hydrocarbon containing from 1 to 30 or more carbon atoms. In some embodiments, the alkyl group may contain 1, 2, or 3 up to 4, 5, 6, 7, 8, 9, 10, 11, 12, 13, 14, 15, 16, 17, 18, 19, 20, 21, 22, 23, 24, 25, 26, 27, 28, 29, or 30 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups such as, but not limited to, polyalkylene oxides (such as PEG), halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3.

"Alkenyl" as used herein alone or as part of another group, refers to linear ("straight chain"), branched chain, and/or cyclic containing from 1 to 30 or more carbon atoms (or in loweralkenyl 1 to 4 carbon atoms) which include 1 to 10 or more double bonds in the hydrocarbon chain. In some embodiments, the alkenyl group may contain 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms. Representative examples of alkenyl include, but are not limited to, methylene (=CH$_2$), vinyl (—CH=CH$_2$), allyl (—CH$_2$CH=CH$_2$), 2-butenyl, 3-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups such as those described in connection with alkyl and loweralkyl above.

"Conjugated," as used herein, refers to a moiety or compound comprising at least two double bonds. In some embodiments, a substrate of the present invention may be conjugated. In certain embodiments, a conjugated moiety or compound may be aromatic. The term "aryl" is used herein to refer to an aromatic moiety or compound. "Aryl" may be a single aromatic ring or multiple aromatic rings that are fused together, linked covalently, or linked to a common group, such as, but not limited to, a methylene or ethylene moiety. The common linking group also may be a carbonyl, as in benzophenone, or oxygen, as in diphenylether, or nitrogen, as in diphenylamine. The term "aryl" specifically encompasses heterocyclic aromatic compounds. The aromatic ring(s) may comprise phenyl, naphthyl, tetrahydronaphthyl, biphenyl, azulenyl, indanyl, indenyl, diphenylether, diphenylamine and benzophenone, among others. In particular embodiments, the term "aryl" means a cyclic aromatic comprising about 5 to about 50 or more carbon atoms, and includes 5- and 6-membered hydrocarbon and heterocyclic aromatic rings. In some embodiments, a substrate of the present invention is aromatic.

"Multiamine," as used herein, refers to a compound comprising two or more amines. A multiamine may comprise 2, 3, 4, 5, 6, 7, or more amines. In some embodiments, a multiamine comprises 2 amines and thus is a diamine. Exemplary multiamines include, but are not limited to, hydrazine, triaminobenzene, ethylenediamine, and any combination thereof.

"Monocarbonyl compound," as used herein, refers to a compound comprising only one carbonyl group. A monocarbonyl compound can comprise an aldehyde (i.e., a monoaldehyde) or a ketone (i.e., a monoketone). In some embodiments, a monocarbonyl compound has the following structure

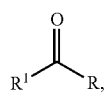

wherein
R is a conjugated or aromatic moiety; and
R$^1$ is selected from the group consisting of hydrogen, alkyl, and an alkylene.

According to some embodiments of the present invention, provided herein are substrates that may be used to prepare a conjugated polymer. "Substrate," as used herein, refers to a compound that can be polymerized to form a polymer. A substrate may be polymerized using chemical oxidative polymerization and/or enzymatic oxidative polymerization. In some embodiments, a substrate may be acted on by an enzyme. For example, a substrate may be oxidized by an enzyme. In other embodiments, a substrate may not be acted on by an enzyme. In some embodiments, a substrate may be polymerized using an oxidizing agent. A substrate may be a synthetic substrate or a natural substrate, either of which may be polymerized using chemical oxidative polymerization and/or enzymatic oxidative polymerization.

"Synthetic," as used herein in reference to a substrate, refers to a substrate that is not a natural substrate of an oxidase. Thus, a synthetic substrate is not found in nature as a substrate for an oxidase and thus is an unnatural substrate. In some embodiments, a synthetic substrate may be synthetically prepared, and optionally one or more compounds may be obtained or derived from nature and used to synthetically prepare a synthetic substrate.

"Natural," as used herein in reference to a substrate, refers to a substrate that is a natural substrate of an oxidase. Thus, a natural substrate is found in nature as a substrate for an oxidase. In some embodiments, a natural substrate may be synthetically prepared, and optionally one or more compounds may be obtained or derived from nature and used to synthetically prepare a natural substrate.

"Organic," as used herein, refers to a compound, substrate, and/or polymer comprising carbon. In some embodiments, an organic substrate may comprise a metal, such as, but not limited to copper, gold, aluminum, lithium, calcium, sodium, tungsten, zinc, iron, platinum, tin, lead, titanium, potassium, silver, rubidium, and any combination thereof. In certain embodiments, an organic substrate is exposed, contacted, and/or doped with a metal and/or metal containing compound such that the metal becomes incorporated with the substrate and/or forms a complex with the substrate.

In certain embodiments, a substrate of the present invention is multifunctional. "Multifunctional," as used herein in reference to a substrate, refers to an organic substrate that comprises at least two moieties that are configured to provide polymerization in more than one direction. A multifunctional organic substrate may comprise 2, 3, 4, 5, or more moieties that may be the same and/or different. In some embodiments, a multifunctional substrate may be a synthetic substrate. In other embodiments, a multifunctional substrate may be a natural substrate. Exemplary multifunctional organic substrates include, but are not limited to, those shown in Scheme 1.

Scheme 1: Exemplary multifunctional organic substrates comprising two, three, or four moieties for polymerization.

1.

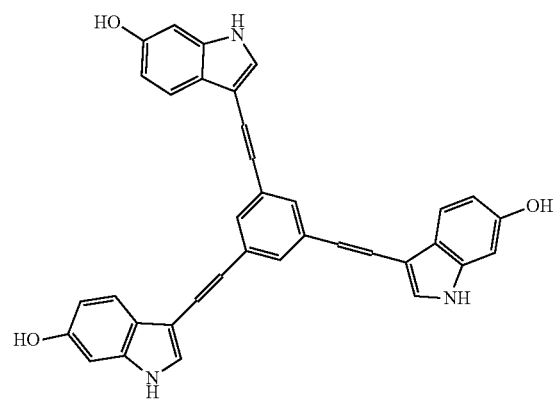

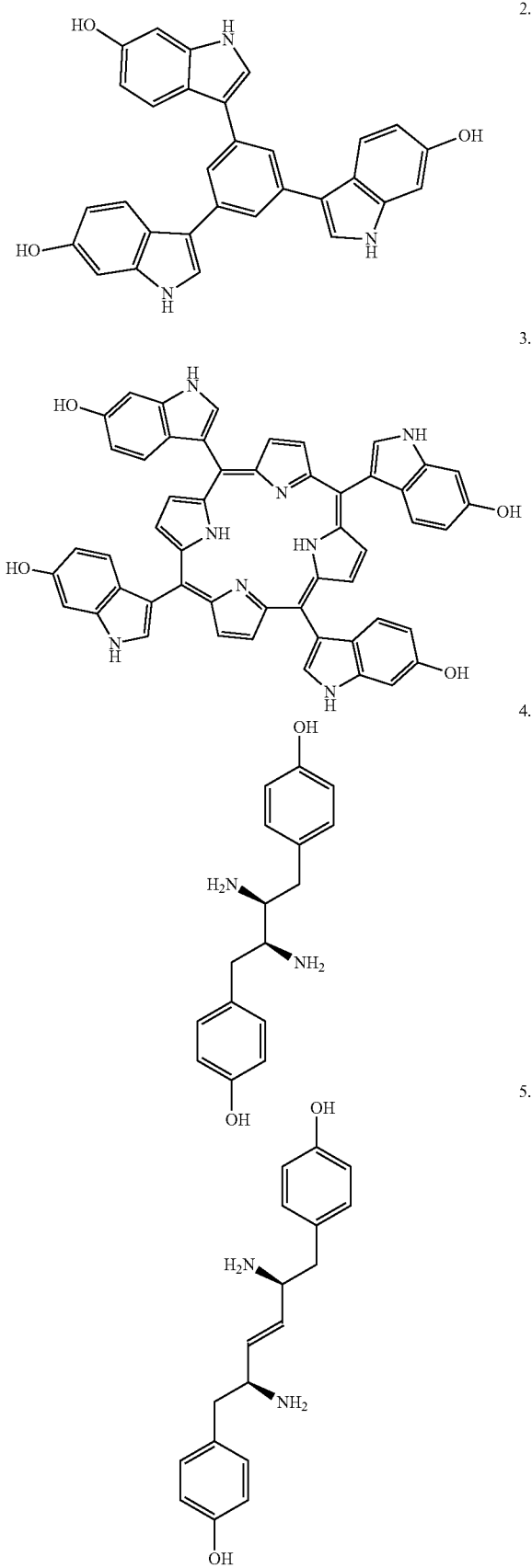
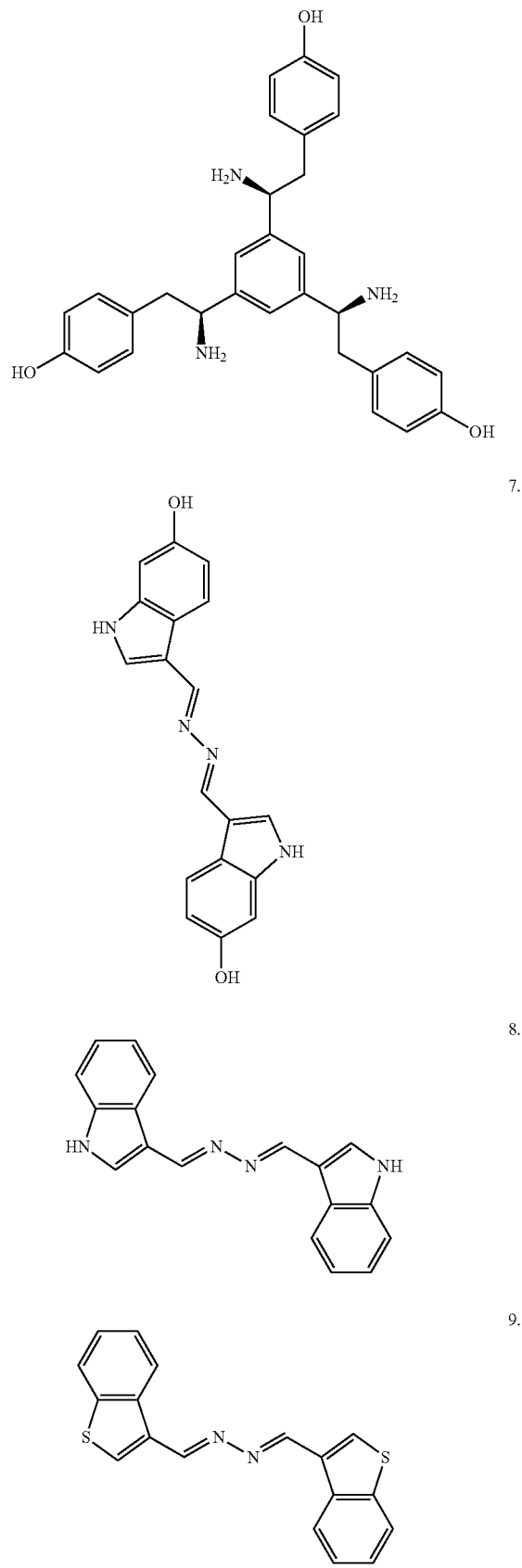

-continued

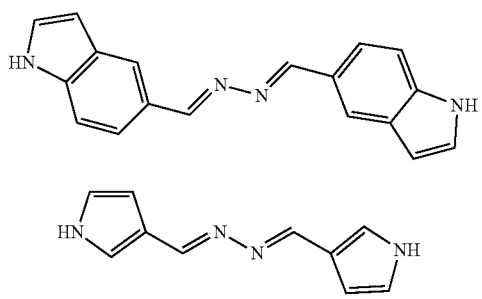

10.

11.

In some embodiments, a multifunctional organic substrate comprises at least two reactive moieties. In certain embodiments, a multifunctional organic substrate comprises at least three reactive moieties. "Reactive moiety" and "reactive moieties," as used herein, refer to moieties that can be oxidized by an oxidase and/or an oxidizing agent. Exemplary reactive moieties include, but are not limited to, an indole, a pyrrole, a catechol, a tyrosyl, a catecholamine, and any combination thereof. In certain embodiments, a substrate comprises one or more reactive moieties selected from the group consisting of a 6-hydroxyindole, a 5-hydroxyindole, a 5,6-dihydroxyindole, and any combination thereof.

In certain embodiments, a reactive moiety may comprise a conjugated moiety. A substrate of the present invention may comprise one or more, such as 2, 3, 4, or more, reactive moieties each of which may comprise a conjugated moiety. In some embodiments, a reactive moiety may comprise an aromatic moiety. A substrate of the present invention may comprise one or more, such as 2, 3, 4, or more, reactive moieties each of which may comprise an aromatic moiety.

As those skilled in the art will recognize, a polymerization reaction may occur or involve one or more reactive sites within a moiety. Thus, a reactive moiety may have at least 2, 3, 4, 5, 6, 7, 8, 9, 10, or more reactive sites. For example, as shown in Scheme 2, for 5,6-dihydroxyindole, polymerization may occur or take place at the C2, C3, C4, and/or C7 position, and a bond may be created between at least one of these reactive sites and at least one reactive site of another reactive moiety.

Scheme 2: Chemical structure of 5,6-dihydroxyindole.

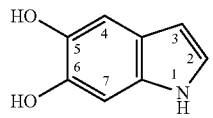

A reactive site within a moiety of a substrate of the present invention may be modified and/or blocked with a substituent, such as, but not limited to an alkyl. This may cause a polymerization reaction to occur or involve one or more different reactive sites within a reactive moiety of a substrate.

A substrate of the present invention may comprise two or more reactive moieties that may be joined by a linker. "Linker" as used herein refers to a moiety that serves as a point of attachment for two or more reactive moieties that may be same and/or different. Two or more reactive moieties may be bound covalently to a linker or may be fused to a linker. A linker may be a conjugated moiety, and in some embodiments a linker may be an aromatic moiety. In certain embodiments, a method of the present invention may result in a linker becoming conjugated. For example, polymerization of a substrate using either an oxidase or an oxidizing agent may result in a conjugated linker.

In some embodiments, a substrate of the present invention is monomeric. "Monomeric," as used herein in reference to a substrate, refers to a substrate that has not been linked or bound to another substrate. Thus, the substrate is not oligomeric or polymeric. While a substrate may have one or more of the same moieties within the substrate, a monomeric substrate does not comprise two or more substrates that have been linked together. For example, the substrates provided in Scheme 1 are monomeric as they have not been linked to another substrate.

In some embodiments, a substrate of the present invention comprises a substrate as described herein. In certain embodiments, a substrate of the present invention comprises a substrate provided in Scheme 1 and/or a substrate described in the examples provided herein. A substrate of the present invention may be used to prepare a polymer of the present invention. In some embodiments, a polymer of the present invention comprises a polymer as described herein. In certain embodiments, a polymer of the present invention comprises a polymer described in the examples provided herein, such as, but not limited to, a polymer provided in Table 2. A method of the present invention may be used to prepare a polymer of the present invention. In some embodiments, a substrate of the present invention may be used in a method of the present invention to prepare a polymer of the present invention.

According to some embodiments of the present invention, a method of preparing an organic polymer is provided, the method comprising polymerizing a multifunctional synthetic organic substrate with an oxidase to form the organic polymer. "Oxidase," as used herein, refers to an enzyme that oxidizes a substrate. Exemplary oxidases include, but are not limited to, phenol oxidase, a polyphenol oxidase, a catechol oxidase, a tyrosinase, a laccase, monophenol monooxygenase, phenolase, monophenol oxidase, cresolase, monophenolase, tyrosine-dopa oxidase, monophenol monooxidase, monophenol dihydroxyphenylalanine:oxygen oxidoreductase, N-acetyl-6-hydroxytryptophan oxidase, dihydroxy-L-phenylalanine oxygen oxidoreductase, o-dipheno:$O_2$ oxidoreductase, catecholase, o-diphenol oxidase, monophenol oxidase, cresolase, and any combination thereof.

In some embodiments, a method of the present invention may comprise polymerizing a multifunctional synthetic organic substrate comprising at least two reactive moieties with an oxidase to form an organic polymer. In certain embodiments, a method of the present invention may comprise polymerizing a multifunctional synthetic organic substrate comprising at least three reactive moieties with an oxidase to form an organic polymer. When a multifunctional synthetic organic substrate comprises at least two reactive moieties, a networked organic polymer may be formed. "Networked," as used herein in reference to a polymer of the present invention, refers to a cross-linked polymer (i.e., a polymer comprising one or more polymer chains that are linked together either directly through covalent attachment and/or through a moiety or group), wherein the polymer chains are interconnected at two or more locations within the polymer chains. In some embodiments, the cross-links (i.e., the linkages connecting the one or more polymer chains) in a networked polymer of the present invention comprise a conjugated moiety.

A method of the present invention may comprise co-polymerizing a multifunctional synthetic organic substrate with an additional substrate using an oxidase to form an organic polymer. The additional substrate may be any organic compound. In some embodiments, an additional substrate may comprise a natural substrate of an oxidase. In some embodiments, an additional substrate may comprise multifunctional organic substrate, such as, but not limited to, a different multifunctional synthetic organic substrate. Thus, the formed organic polymer may comprise one or more different units.

Prior to or concurrently with the polymerizing step, a metal may be added to the substrate and/or reaction mixture. Thus, a substrate and/or organic polymer may be doped with a metal, ionic liquid, ionomer, and/or other dopant(s). In some embodiments, a dopant may oxidize or reduce the conjugated polymer. In some embodiments, doping a substrate and/or organic polymer may increase the electrical properties of the organic polymer.

In certain embodiments, after the polymerizing step, the organic polymer may be reacted with an oxidizing agent. This may provide further cross-linking in the organic polymer. Exemplary oxidizing agents include, but are not limited to, ammonium persulfate, iron (III) chloride, hydrogen peroxide, urea peroxide, melamine peroxide, sodium perborate, potassium perborate, sodium percarbonate, potassium percarbonate, potassium persulfate, sodium persulfate, ferric nitrate, diammonium cerium nitrate, iron sulfate, ozone, potassium periodate, and any combination thereof. In some embodiments, an organic substrate may be co-reacted with the organic polymer and oxidizing agent. The organic substrate according to some embodiments may comprise a multifunctional organic substrate.

According to further embodiments of the present invention, provided is a method of preparing an organic polymer, the method comprising polymerizing a multifunctional organic substrate with an oxidizing agent to form said organic polymer. Exemplary oxidizing agents for us in the method include, but are not limited to, those described herein. In some embodiments, a method of the present invention may comprise polymerizing a multifunctional organic substrate comprising at least two reactive moieties with an oxidase to form an organic polymer. In certain embodiments, a method of the present invention may comprise polymerizing a multifunctional organic substrate comprising at least three reactive moieties with an oxidase to form an organic polymer. When a multifunctional organic substrate comprises at least two reactive moieties, a networked organic polymer may be formed.

A method of the present invention may comprise co-polymerizing a multifunctional organic substrate with an additional substrate using an oxidizing agent to form an organic polymer. The additional substrate may be any organic compound. In some embodiments, an additional substrate may comprise a natural substrate of an oxidase. In some embodiments, an additional substrate may comprise a different multifunctional organic substrate. Thus, the formed organic polymer may comprise one or more different units.

Prior to or concurrently with the polymerizing step, a metal may be added to the substrate and/or reaction mixture. Thus, a substrate and/or organic polymer may be doped with a metal, ionic liquid, ionomer, and/or other dopant(s). In some embodiments, a dopant may oxidize or reduce the conjugated polymer. In some embodiments, doping a substrate and/or organic polymer may increase the electrical properties of the organic polymer.

In certain embodiments, after the polymerizing step, the organic polymer may be reacted a second time with an oxidizing agent. This may provide further cross-linking in the organic polymer. In some embodiments, an organic substrate may be co-reacted with the organic polymer and oxidizing agent. The organic substrate according to some embodiments may comprise a multifunctional organic substrate.

In some embodiments, a method of the present invention may comprise polymerizing a synthetic organic substrate comprising an aldehyde, such as, but not limited to, at least two or three aldehydes, with an oxidase to form an organic polymer, then reacting the organic polymer with a multiamine to cross-link the organic polymer. As those skilled in the art will recognize, an organic polymer may already comprise cross-links and thus the reacting step may comprise providing further or additional cross-links within the organic polymer. In certain embodiments, a networked polymer may be formed.

In some embodiments, a method of the present invention may comprise polymerizing a synthetic organic substrate comprising a ketone, such as, but not limited to, at least two or three ketones, with an oxidase and/or oxidizing agent to form an organic polymer, then reacting the organic polymer with a multiamine to cross-link the organic polymer. As those skilled in the art will recognize, an organic polymer may already comprise cross-links and thus the reacting step may comprise providing further or additional cross-links within the organic polymer. In certain embodiments, a networked polymer may be formed.

According to an additional embodiment of the present invention, provided is a method of preparing a cross-linked polayzine polymer comprising reacting an organic substrate comprising at least two aldehydes and/or ketones with a multiamine to form an organic polymer, and oxidizing said organic polymer to form said cross-linked polyazine polymer. The oxidizing step may be carried out by enzymatic oxidative polymerization with an oxidase and/or by chemical oxidative polymerization with an oxidizing agent. The organic substrate may be a natural or synthetic substrate.

An organic substrate comprising at least two aldehydes and/or ketones may comprise a conjugated moiety. In some embodiments, an organic substrate comprising at least two aldehydes and/or ketones may comprise an aromatic moiety. Optionally, the at least two aldehydes and/or ketones may be attached and/or bound to the aromatic moiety. In some embodiments, an organic substrate has the structure

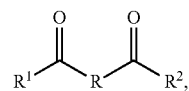

wherein

R is a conjugated or aromatic moiety; and $R^1$ and $R^2$ are each independently selected from the group consisting of hydrogen, alkyl, and alkenyl, and the organic polymer has a structure comprising $(RCNNC)_nRC(O)R^1$, $(RCNNC)_nRC(O)R^2$, or $(RCNNC)_nCNN$, wherein n is a number from 2 to 1,000,000.

An organic substrate according to some embodiments may comprise at least three aldehydes and/or ketones, and may in some embodiments react with a multiamine to form a networked organic polymer. In some embodiments, an organic substrate has the structure

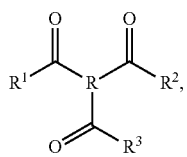

wherein

R is a conjugated or aromatic moiety; and $R^1$, $R^2$, and $R^3$ are each independently selected from the group consisting of hydrogen, alkyl, and alkenyl, and wherein the organic polymer has a structure comprising $(RC_3N_3N_3C_3)_nRC(O)R^1$, $(RC_3N_3N_3C_3)_nRC(O)R^2$, $RC_3N_3N_3C_3)_nRC(O)R^3$, or $(RC_3N_3N_3C_3)_nCNN$, wherein n is a number from 2 to 1,000,000.

In certain embodiments, an organic substrate may comprise an indole, a pyrrole, a phenol, a thiophene, a furan, a thianaphthene, an acetylene, a catechol, a tyrosyl, a catecholamine, and any combination thereof. In some embodiments, an organic substrate comprises an indole or a pyrrole that may be substituted with at least two aldehydes and/or ketones.

Prior to the oxidizing step, a method of preparing a cross-linked polyazine polymer may comprise reacting the organic polymer with a second organic substrate comprising at least two aldehydes and/or ketones and a multiamine. In some embodiments, the second organic substrate is different than the first organic substrate and thus a heteropolymer is formed. "Heteropolymer" as used herein refers to an organic polymer comprising two or more different polymeric units.

Prior to or concurrently with one or more steps in a method of preparing a cross-linked polyazine polymer, a metal may be added to the substrate and/or reaction mixture. Thus, a substrate, organic polymer, and/or cross-linked polyazine polymer may be doped with a metal, ionic liquid, ionomer, and/or the like. In some embodiments, doping a substrate, organic polymer, and/or cross-linked polyazine polymer with a metal may increase the electrical properties of the organic polymer. In certain embodiments, the oxidizing step is carried out with a reagent, such as, but not limited to, iron (III) chloride, that may oxidize the organic polymer and dope the organic polymer and/or cross-linked polyazine polymer with a metal.

In some embodiments, a method of preparing a cross-linked polyazine polymer may comprise reacting a monocarbonyl compound with the organic polymer and a multiamine prior to the oxidizing step. Reaction of the organic polymer with a multiamine and monocarbonyl compound can result in a capped organic polymer, meaning that the monocarbonyl compound may be added onto the end of one or more of the polymer chains. In some embodiments, a monocarbonyl compound has the structure

wherein

R is a conjugated or aromatic moiety; and $R^1$ is selected from the group consisting of hydrogen, alkyl, and alkenyl.

A substrate of the present invention and/or a method of the present invention may provide a conjugated organic polymer and/or a cross-linked polyazine polymer.

According to further embodiments of the present invention, provided is an electrochemical device comprising an organic polymer and/or a cross-linked polyazine polymer of the present invention. An electrochemical device according to embodiments of the invention may comprise a working electrode, a counter electrode, and an organic polymer and/or cross-linked polyazine polymer of the present invention, wherein said working electrode is in operative communication with said counter electrode, and the organic polymer and/or cross-linked polyazine polymer is in operative communication with said working electrode or said counter electrode. In certain embodiments, the organic polymer and/or a cross-linked polyazine polymer may be conjugated, and may optionally comprise a metal.

In some embodiments, an organic polymer and/or cross-linked polyazine polymer of the present invention is disposed on at least a portion of a working electrode. The organic polymer and/or cross-linked polyazine polymer may be directly or indirectly in contact with at least a portion of a working electrode. In certain embodiments, an organic polymer and/or cross-linked polyazine polymer of the present invention may be interposed between a working electrode and a counter electrode. In some embodiments, an electrochemical device comprises an organic polymer and/or cross-linked polyazine polymer of the present invention that may be in the form of a coating in contact with or on a working electrode and/or a counter electrode.

An electrochemical device of the present invention encompasses all types of devices to perform electrochemical reactions. Exemplary electrochemical device include, but are not limited to, a battery, a fuel cell, a solar cell, a capacitor or a device formed of a combination thereof, a supercapacitor, an ultracapacitor, an electric double-layer capacitor, and any combination thereof.

The present invention is explained in greater detail in the following non-limiting Examples.

EXAMPLES

Example 1

All reactions were carried out in approximately 50 mM potassium phosphate buffer, pH 6.5 with approximately 5 mM substrate and mushroom tyrosinase (polyphenol oxidase) Sigma T3824 in an amount of 100 to 10,000 units. Reaction volumes varied from 200 μl to 2 ml. In cases where substrates were not completely solubilized, then a saturated solution was used as the limit of solubility. In some cases, a solution of DMSO was used to increase solubility of the substrates. The enzyme was tested and shown to retain activity up to 50% DMSO. These cases are indicated in Table 1. The reactions were observed over a 24 hour period for the production of polymers, and the presence and color of polymer and solution was recorded.

The production of polymers in each reaction was visible as a precipitate in the well of a 96 well plate or in the reaction mixture on a glass slide.

TABLE 1

Testing of polymer production in enzymatic tyrosinase (polyphenyl oxidase) reaction.

| | Result | Notes |
|---|---|---|
| Substrate Tested | | |
| Tyrosine* | ++ | Black powdery polymer precipitate |
| N-methyl tyrosine | ++ | Black powdery polymer precipitate, N can be blocked. |
| Tyramine* | +++ | Black sticky polymer precipitate. Forms faster than tyrosine. Some iridescence in films formed at surface. |
| Tyramine HCl* | +++ | Black brown sticky polymer precipitate. Forms faster than tyrosine. Some iridescence. |
| 5-hydroxyindole* | +++ | Black polymer precipitate. |
| 6 Hydroxyindole | ++ | Black polymer precipitate. |
| 2 Hydroxy carbazole** | − | Darker brown than control but no clear polymer. May be quinone. |
| Harmalol HCl dehydrate** | − | No reaction. |
| Indole | − | No reaction. |
| Beta phenylethylamine HCL | +/− | Some white precipitate, may be polymer or compound coming out of solution. |
| Crosslinking Substrates Tested | | |
| 1,3,5 Tris(4hydroxyphenyl)benzene (20% DMSO) | + | Cloudy precipitate with a slight brown/orange color in solution. Color may indicate the quinone. |
| 2,6 dihydroxnaphthalene | + | Some precipitate, may be polymer or compound coming out of solution. After 24 hours there was some dark color to the polymer indicating some polymer formed. |
| Mixtures tested | | |
| Tyrosine + Tyramine | +++ | Black polymer precipitate. |
| Tyrosine + 2-Hydroxy carbazole** | +++ | Black polymer precipitate. |
| Tyrosine + Harmalol HCl** | +++ | Reacts faster than Tryosine alone, harmalol may be incorporated as a reactant. |
| Tyrosine + 1,3,5-Tris (4-hydroxyphenyl) benzene** | +++ | Black polymer precipitate. |
| Tyramine + 2-Hydroxy carbazole** | +++ | Black polymer precipitate. |
| Tyramine + Harmalol HCl** | +++ | Reacts faster than Tryosine alone, harmalol may be incorporated as a reactant. |
| Tyramine + 1,3,5-Tris (4-hydroxyphenyl) benzene** | +++ | Black polymer precipitate. |
| 2-Hydroxy carbazole** + Harmalol HCl** | + | Fine dark precipitate |
| 2-Hydroxy carbazole** + 1,3,5-Tris (4-hydroxyphenyl) benzene** | − | |
| Harmalol HCl + 1,3,5-Tris (4-hydroxyphenyl) benzene** | − | |

*Reported substrate for phenol oxidases.
**Dissolved in 20% DMSO.
+++ Reacted within about 1 hour;
++ reacted within about 3 hours;
+ reacted within about 24 hours;
+/− inconclusive results;
− no reaction.

Example 2

Creation of Networked Polymer Sheets with Compound 2

In 50 μl of DMSO, 10 mg of compound 2 (Scheme 3) was dissolved and added to 10 mg of either indole, 5-hydroxyindole, 6-hydroxyindole, or serotonin that was dissolved in 50 μl DMSO.

Scheme 3: Chemical structure of compound 2.

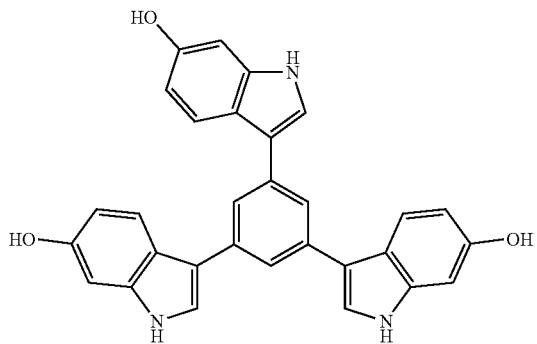

The samples were polymerized by oxidation with 100 μl of 0.8 M ammonium persulfate in water in the case of indole and 5-hydroxyindole and 100 μl of 0.2 M ammonium persulfate in water in the case of 6-hydroxyindole and serotonin. These were compared to solutions of 50 μl 5-hydroxyindole, 6-hydroxyindole, and serotonin polymerized with equal volumes of the same concentrations of ammonium persufate without compound 2. Sheets of networked polymer were produced and examined microscopically at 200× and 400× magnification as shown in FIGS. 1A-D. 6-hydroxyindole did not network into a polymer sheet under these conditions. Controls of indole, 5-hydroxyindole and 6-hydroxyindole alone only formed amorphous dark particulate precipitates.

Example 3

Polyazine polymers were synthesized as follows. 0.2 g of various dicarboxaldehydes were reacted with 0.03 g of hydrazine monohydrate (65%) or triaminobenzene in 15 ml of ethanol or acetonitrile to yield azadiene polymers (Table 2). In some cases, as with ketones, the PH was adjusted to about 5.0. In some cases these polymers were further modified (i.e., capped) by addition of indole or pyrrole moieties on the ends of the polymer chain by reacting the washed azadiene polymer with an 0.1 g of indole aldehydes or pyrrole aldehydes and 0.015 g of hydrazine monohydrate (15%) in 5 ml of ethanol or acetonitrile as described in Table 2. These resulted in capped polymers with the ends capped with one or more indole or pyrrole groups. Some of the capped polymers were subsequently crosslinked with an excess of 0.8 M ammonium persulfate.

Figure 2:
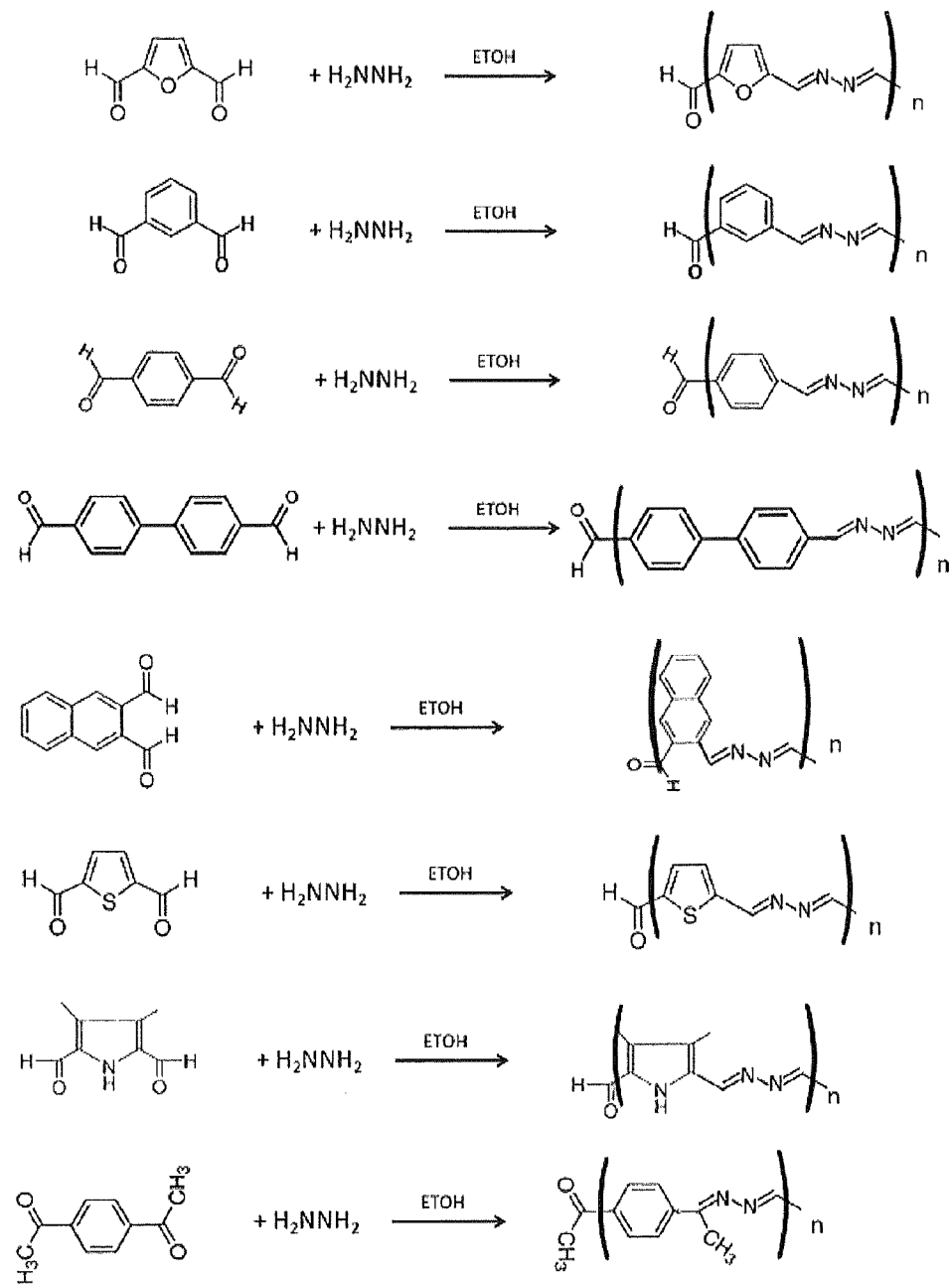
FIG. 2 shows the synthesis of the following azadiene polymers (from top to bottom): 2,5-furan azadiene polymer, benzene-1,3-azadiene polymer, benzene-1,4-azadiene polymer, 4,4-biphenyl azadiene polymer, 2,3-naphthalene azadiene polymer, 2,5-thiophene azadiene polymer, 3,4-dimethyl-2,5-pyrrole azadiene polymer, and benzene-1,4-methyl azadiene polymer.
Figure 3:
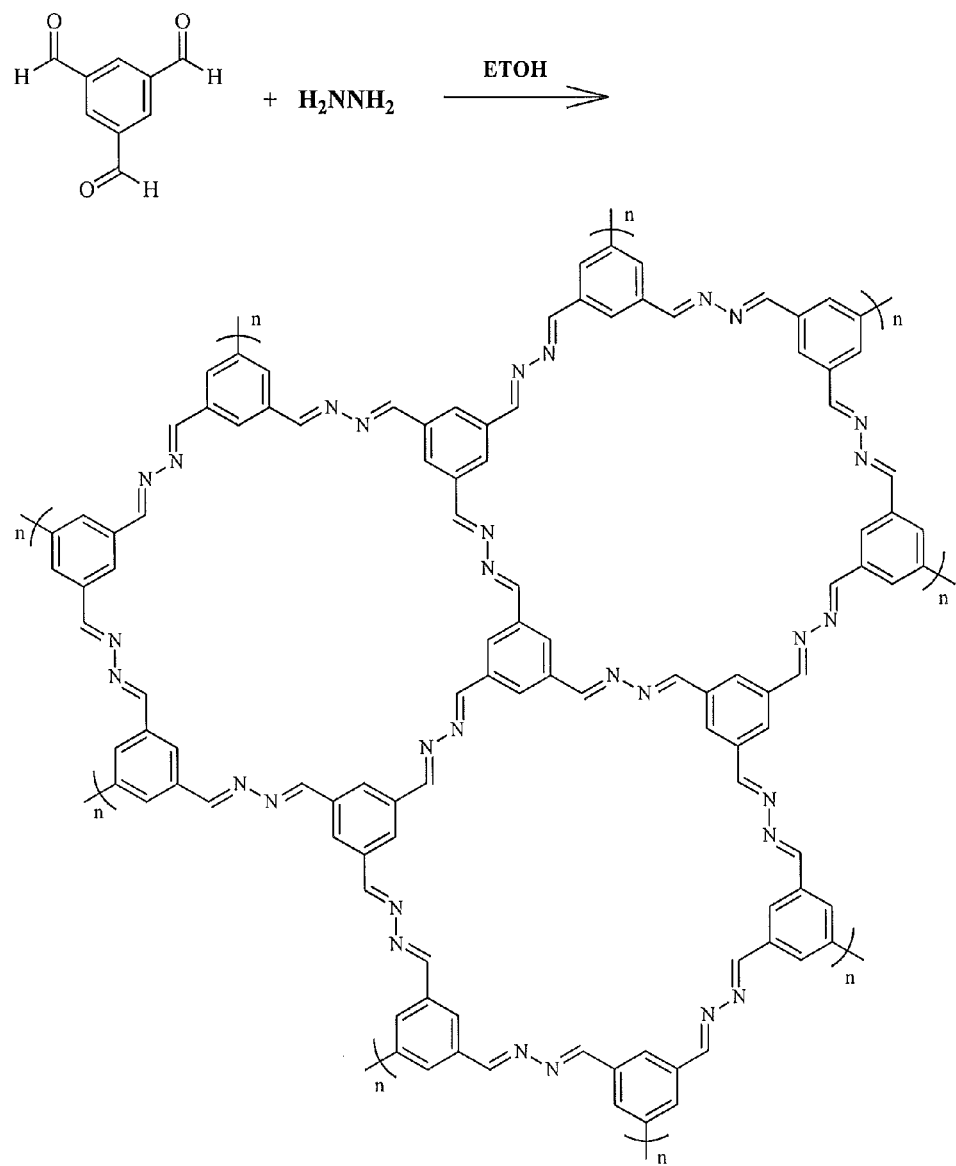
FIG. 3 shows the synthesis of a networked benzene-1,3,5-azadiene polymer using 1,3,5 benzene tricarboxaldehyde and hydrazine.
Figure 4:
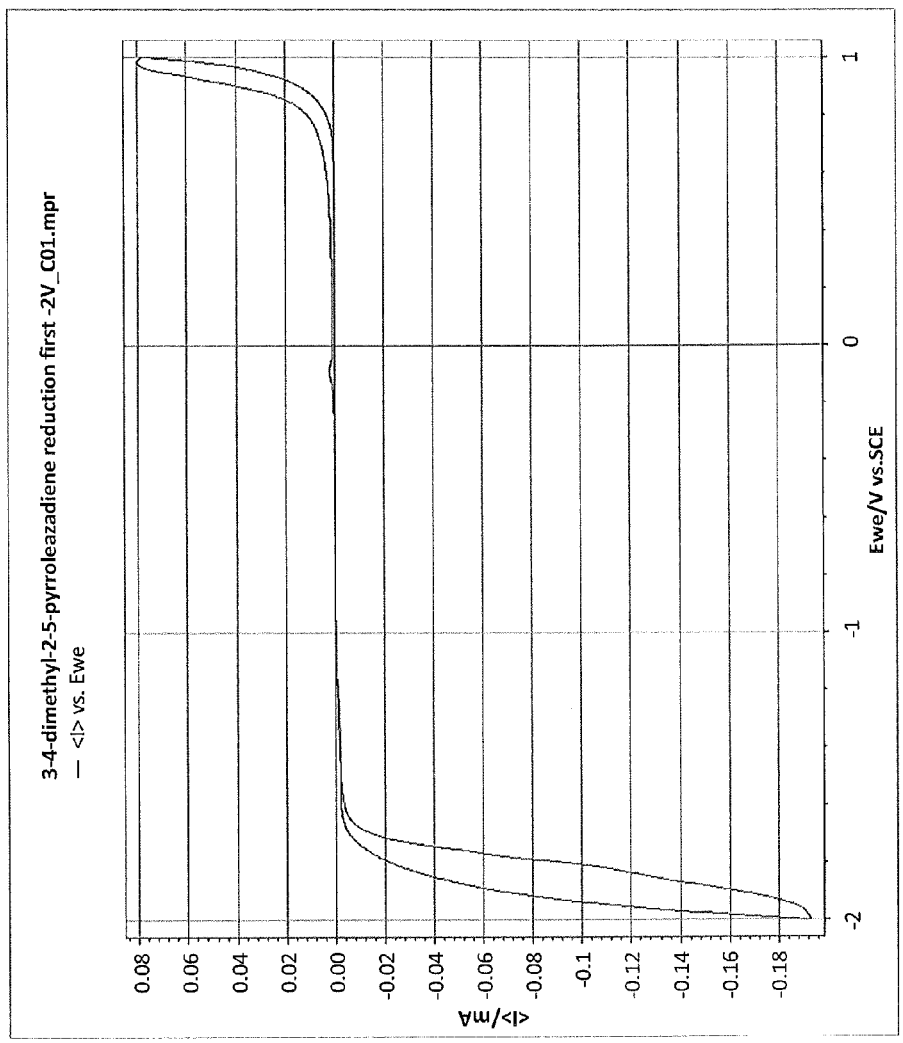
FIG. 4 shows a cyclic voltammetery of 3,4 dimethyl pyrrole azadiene linear conjugated polymer.

FIG. 2 shows the synthesis of the azadiene polymers. FIG. 3 shows the synthesis of a networked benzene-1,3,5-azadiene polymer using 1,3,5 benzene tricarboxaldehyde and hydrazine. FIG. 4 shows a cyclic voltammetery of 3,4 dimethyl pyrrole azadiene linear conjugated polymer.

TABLE 2

Synthetic details for preparing polyazine polymers.

| Reactant 1 | Reactant 2 | Solvent | Product | Capping Reactant 1 | Capping reactant 2 | Solvent | Product | Cross-linking reactant |
|---|---|---|---|---|---|---|---|---|
| 2,5-furan dicarboxaldehyde | Hydrazine | Ethanol | 2,5-furan azadiene polymer | | | | | |
| 2,5-furan dicarboxaldehyde | Hydrazine | Ethanol | 2,5-furan azadiene polymer | Indole-5-carboxaldehyde | Hydrazine | acetonitrile | Indole capped furan-2,5,-azadiene polymer | Ammonium persulfate |
| 2,5-furan dicarboxaldehyde | Hydrazine | Ethanol | 2,5-furan azadiene polymer | Pyrrole-2carboxaldehyde | Hydrazine | acetonitrile | Pyrrole capped furan-2,5,-azadiene polymer | Ammonium persulfate |
| Benzene-1,3-dicarboxaldehyde | Hydrazine | Ethanol | Benzene-1,3-azadiene polymer | | | | | |
| Benezene-1,4-dicarboxaldehyde | Hydrazine | Ethanol | Benezene-1,4-azadiene polymer | | | | | |
| 4,4-biphenyl dicarboxaldehyde | Hydrazine | Ethanol, acetonitrile | 4,4-biphenyl azadiene polymer | | | | | |
| 2,3-naphthalene dicarboxaldehyde | Hydrazine | Ethanol, acetonitrile | 2,3-naphthalene azadiene polymer | | | | | |
| 2,5-thiophene dicarboxaldehyde | Hydrazine | Ethanol | 2,5-thiophene azadiene polymer | | | | | |
| 3,4-dimethyl-2,5-pyrrole dicarboxaldehyde | Hydrazine | Ethanol | 3,4-dimethyl-2,5-pyrrole azadiene polymer | | | | | |
| Benzene-1,3,5-tricarboxaldehyde | Hydrazine | Ethanol, acetonitrile | Benzene-1,3,5-azadiene network polymer | | | | | |
| Benzene-1,3,5-tricarboxaldehyde | Hydrazine | Ethanol, acetonitrile | Benzene-1,3,5-azadiene network polymer | 5-carboxyindole | Hydrazine | acetonitrile | Indole capped Benzene-1,3,5-azadiene network polymer | |
| Benzene-1,3,5-tricarboxaldehyde | Hydrazine | Ethanol, acetonitrile | Benzene-1,3,5-azadiene network polymer | 5-carboxyindole | Hydrazine | acetonitrile | Indole capped Benzene-1,3,5-azadiene network polymer | Ammonium persulfate |

TABLE 2-continued

Synthetic details for preparing polyazine polymers.

| Reactant 1 | Reactant 2 | Solvent | Product | Capping Reactant 1 | Capping reactant 2 | Solvent | Product | Cross-linking reactant |
|---|---|---|---|---|---|---|---|---|
| Benzene-1,3,5-tricarboxaldehyde | Hydrazine | Ethanol, acetonitrile | Benzene-1,3,5-azadiene network polymer | 5-carboxyindole | Hydrazine | acetonitrile | Indole capped Benzene-1,3,5-azadiene network polymer | Iron Chloride (FeCl$_3$) |
| Benzene-1,3,5-tricarboxaldehyde | Triaminobenzene | Ethanol, acetonitrile | Benzene-imine network polymer | | | | | |
| 1,4-diacetyl benzene | Hydrazine | Ethanol | Benzene-1,4-methyl azadiene polymer | | | | | |
| 1,3,5-triacetyl benzene | Hydrazine | Ethanol, acetonitrile | Benezene-1,3,5-methyl azadiene network polymer | | | | | |

Example 4

A polyazine polymer of furan 2,5-azadiene was synthesized as follows. 0.2 g of furan 2,5-dicarboxaldehyde was reacted with 30 µl of hydrazine monohydrate (65%) in 15 ml of ethanol to yield the furan 2,5-azadiene polymer (Scheme 4).

Scheme 4: Reaction for the furan 2,5-azadiene polymer.

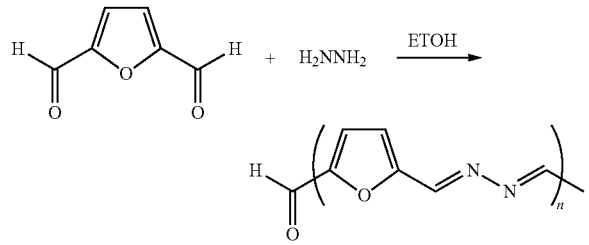

Figure 5:
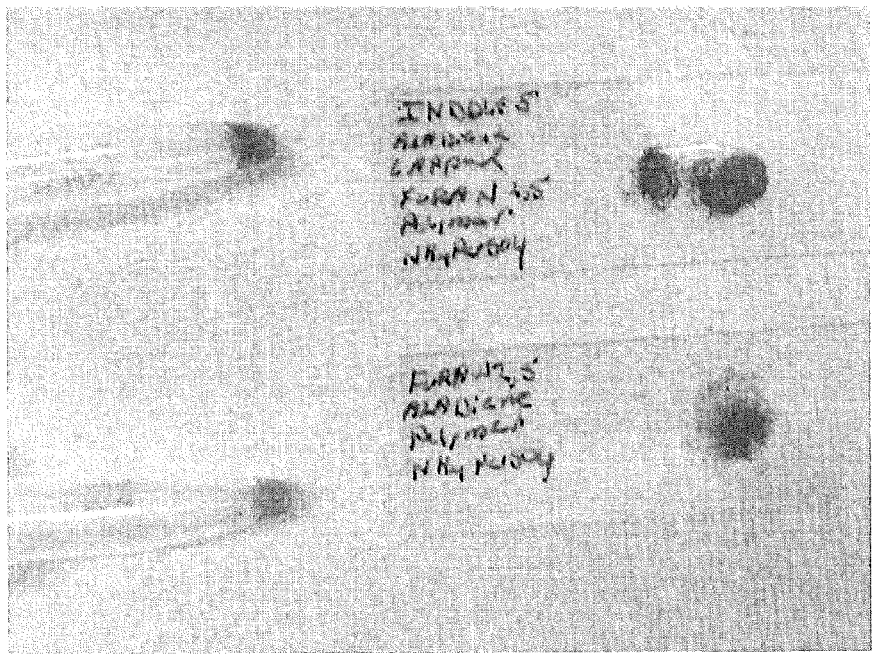
FIG. 5 shows the indole capped 2,5 azadiene polymer polymer (bottom) and the final networked indole capped polymer after oxidation (top).

This polymer was further modified by the addition of indole or pyrrole moieties on the ends of the polymer chain by reacting the ethanol washed polymer (0.05 g) with 0.05 g of indole-5-carboxaldehyde or 0.05 g of pyrrole-2-carboxaldehyde and 12 µl of hydrazine monohydrate (65%) in 5 ml of acetonitrile to yield indole or pyrrole capped polymers respectively. These polymers were subsequently crosslinked into networked lattices by reacting with an excess of 0.8 M ammonium persulfate. FIG. 5 shows the indole capped 2,5 azadiene polymer polymer (bottom) and the final networked indole capped polymer after oxidation (top).

Example 5

Figure 6A:
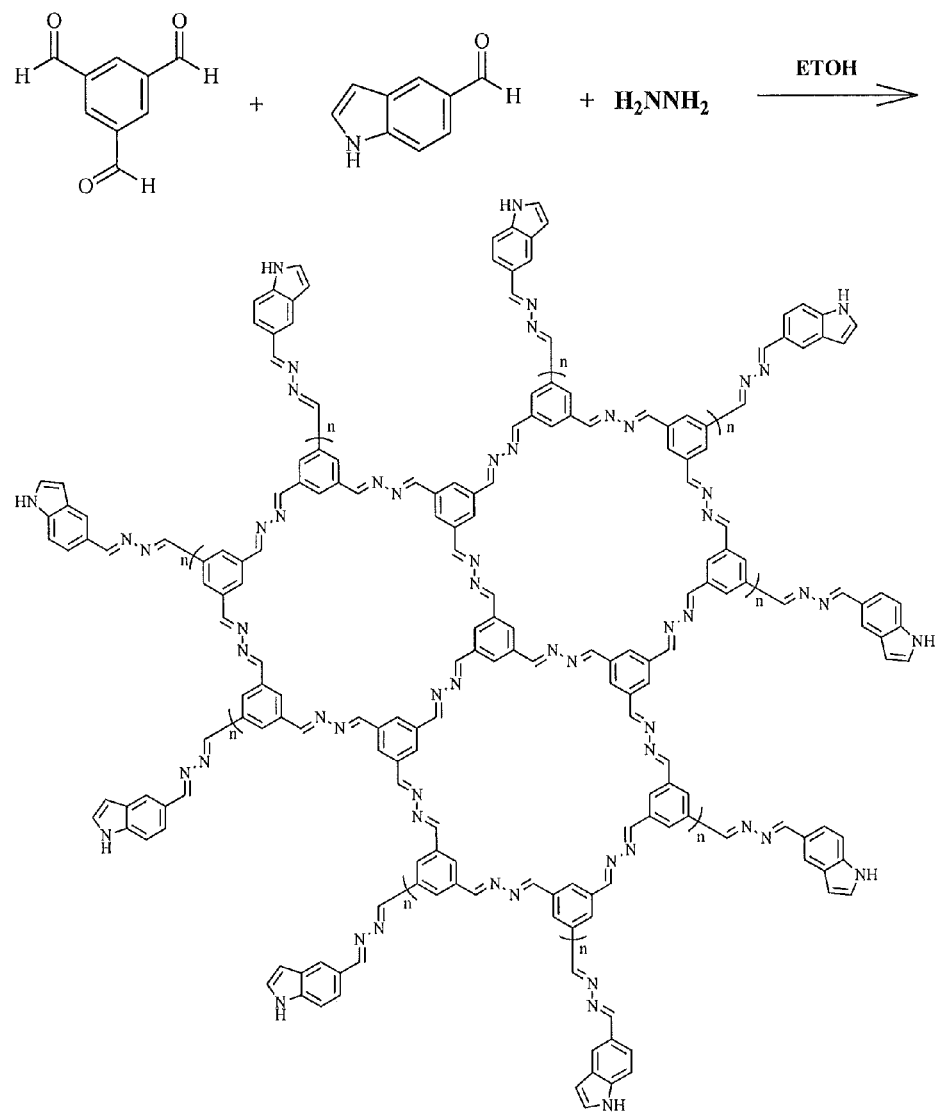
FIG. 6A shows the synthesis of an indole capped benzene-1,3,5-azadiene network polymer.
Figure 6B:
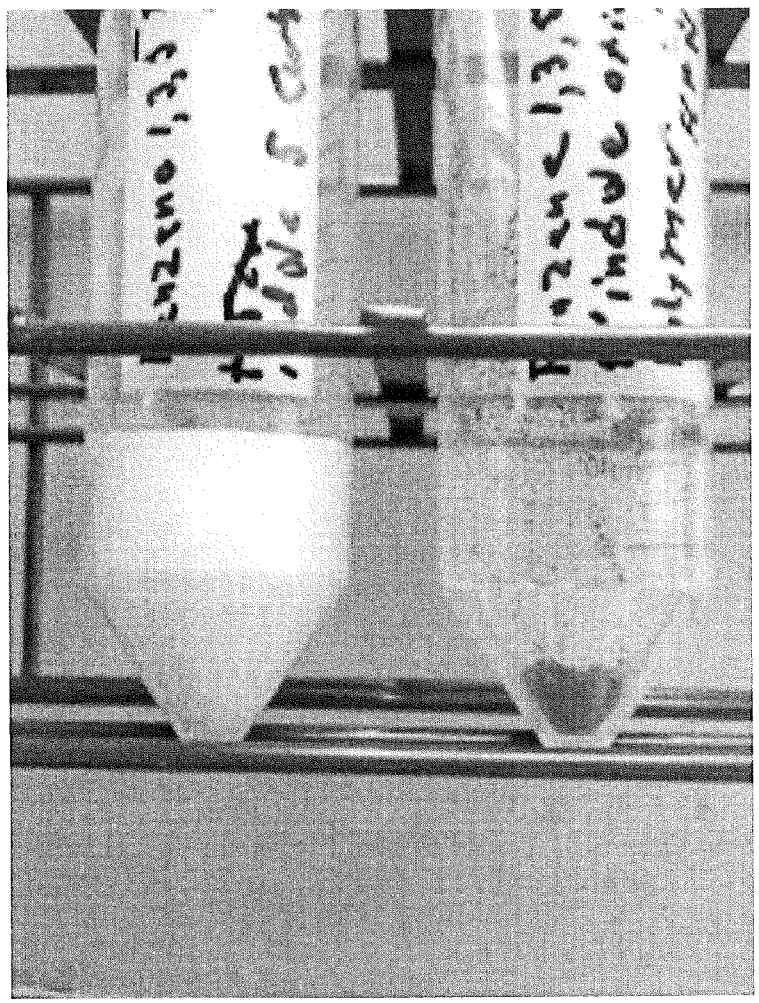
FIG. 6B shows the indole capped benzene-1,3,5-azadiene network polymer prior to oxidation (left) and after oxidation (right) with ammonium persulfate to produce an indole crosslinked benzene 1,3,5-azadiene network polymer.
Figure 6C:
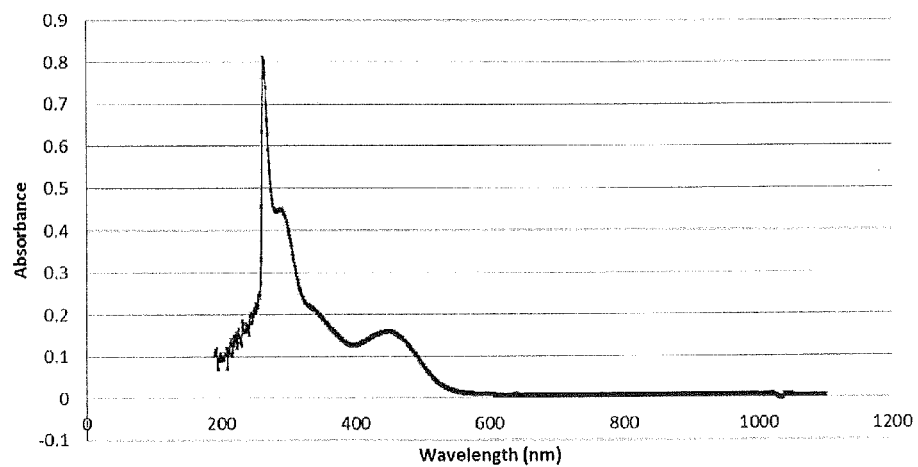
FIG. 6C shows an absorption spectrum for the oxidized cross-linked indole capped 1,3,5 benzene azadiene polymer.
Figure 6D:
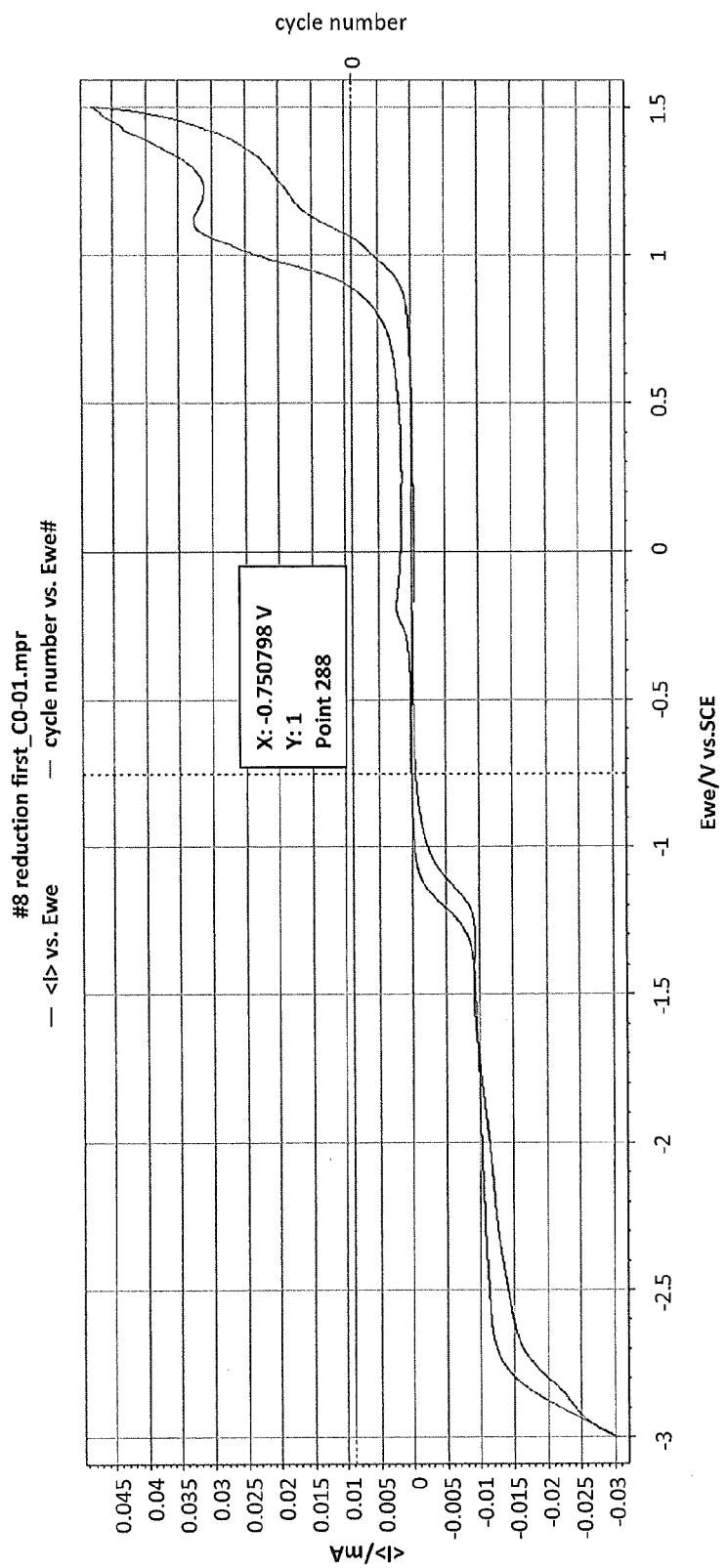
FIG. 6D shows a cyclic voltammetery of the oxidized cross-linked indole capped 1,3,5 benzene azadiene polymer.

An indole capped 1,3,5 benzene azadiene networked polymer was prepared. 0.25 g of 1,3,5 tricarbox-aldehyde was reacted with 100 µl of hydrazine monohydrate (65%) in 10 ml of acetonitrile. To this mixture 1 g of 5-carboxyindole was added to terminate the polymerization reaction while capping the polymer chain extensions. FIG. 6A shows the synthesis of an indole capped benzene-1,3,5-azadiene network polymer, which was subsequently reacted with either ammonium persulfate or FeCl3 oxidizing agents to crosslink the indoles, thereby producing an indole crosslinked benezene 1,3,5-azadiene network polymer. The polymer shifted from a white milky colloidal solution to a deep red/black precipitate upon oxidative cross-linking as shown in FIG. 6B upon oxidation of the polymer with ammonium persulfate. FIG. 6C shows an absorption spectrum for the oxidized cross-linked indole capped 1,3,5 benzene azadiene polymer. Absorption spectrum was determined by dissolving the soluble portion of the oxidized polymer in dimethylformamide and reading absorbance on a Shimadzu UV/Vis mini 1240 from 180 nm to 1100 nm. Cyclic voltammetery was performed to determine HOMO, LUMO and bandgap for the polymer (FIG. 6D). The polymer was heat evaporated onto a glassy carbon electrode and cyclic voltammetry was performed using a Bio-Logics SP150 potentiostat.galvanostat in anhydrous acetonitrile TBAP purged with argon.

Example 6

Multifunctional organic substrates were synthesized as set forth in Table 3.

TABLE 3

Dimer cross-linking substrates.

| Reactant 1 | Reactant 2 | Solvent | Product |
|---|---|---|---|
| Indole-2-carboxaldehyde | Hydrazine | Ethanol | Indole-2-azadiene |
| Indole-5-carboxaldehyde | Hydrazine | Ethanol | Indole-5-azadiene |
| Pyrrole-2-carboxaldehyde | Hydrazine | Ethanol | Pyrrole-2-azadiene |
| Thianaphthene-2-carboxaldehyde | Hydrazine | Ethanol | Thianaphthene-2-azadiene |

Figure 7:
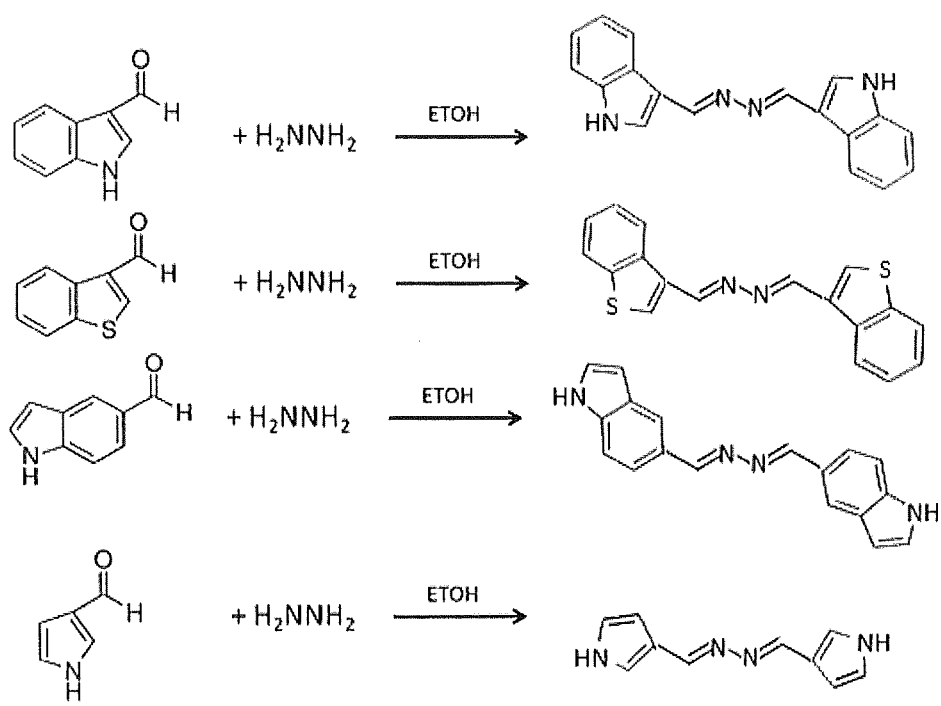
FIG. 7 shows the synthesis of the following multifunctional substrates (from top to bottom): 2-indole azadiene, thianaphthene-2-azadiene, 5-indole azadiene, and 2-pyrrole azadiene.

FIG. 7 shows (from top to bottom) the synthesis of the 2-indole azadiene, thianaphthene-2-azadiene, 5-indole azadiene, and 2-pyrrole azadiene.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A method of preparing a cross-linked polyazine polymer, comprising:
reacting an organic substrate with a multiamine to form an organic polymer, wherein the organic substrate comprises a substituted moiety selected from the group consisting of an indole, pyrrole, phenyl, biphenyl, thiophene, furan, naphthalene, thianaphthene, acetylene, catechol, tyrosyl, and catecholamine, and the organic substrate is substituted with at least two aldehydes and/or ketones; and oxidizing said organic polymer to form said cross-linked polyazine polymer.

2. The method of claim 1, wherein said oxidizing step is carried out by enzymatic oxidative polymerization.

3. The method of claim 1, wherein said oxidizing step is carried out by chemical oxidative polymerization with an oxidizing agent.

4. The method of claim 1, wherein said moiety is substituted with said at least two aldehydes and/or ketones.

5. The method of claim 1, wherein said organic substrate comprises at least three aldehydes and/or ketones.

6. The method of claim 1, wherein said multiamine is selected from the group consisting of hydrazine, triaminobenzene, and any combination thereof.

7. The method of claim 1, wherein said cross-linked polyazine polymer is a heteropolymer.

8. The method of claim 1, further comprising reacting said organic polymer with a second organic substrate comprising at least two aldehydes and/or ketones and a multiamine, prior to said oxidizing step.

9. The method of claim 1, further comprising reacting a monocarbonyl compound with said organic polymer and a multiamine to form a capped organic polymer, prior to said oxidizing step.

10. The method of claim 9, wherein said monocarbonyl compound has the structure

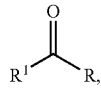

wherein
R is a conjugated or aromatic moiety; and
$R^1$ is selected from the group consisting of hydrogen, alkyl, and alkenyl.

11. The method of claim 1, wherein said organic substrate comprises a metal.

12. An electrochemical device comprising: a working electrode; a counter electrode; and said networked polyazine polymer of claim 1, wherein said working electrode is in operative communication with said counter electrode, and said cross-linked polyazine polymer is in operative communication with said working electrode or said counter electrode.

13. The electrochemical device of claim 12, wherein said cross-linked polyazine polymer is disposed on a least a portion of the working electrode.

14. The electrochemical device of 12, wherein the electrochemical device is a battery, a fuel cell, a capacitor or a device formed of a combination thereof, a supercapacitor, an ultracapacitor, or an electric double-layer capacitor.

15. The method of claim 1, wherein said organic substrate has a structure selected from the group consisting of

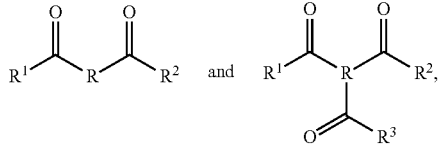

wherein
R is a conjugated moiety selected from the group consisting of an indole, pyrrole, phenyl, biphenyl, thiophene, furan, naphthalene, thianaphthene, catechol, tyrosyl, and catecholamine; and
$R^1$, $R^2$, and $R^3$ are each independently selected from the group consisting of hydrogen, alkyl, and alkenyl.

* * * * *

UNITED STATES PATENT AND TRADEMARK OFFICE
CERTIFICATE OF CORRECTION

PATENT NO. : 9,193,819 B2  
APPLICATION NO. : 14/173269  
DATED : November 24, 2015  
INVENTOR(S) : Duck Page 1 of 1

It is certified that error appears in the above-identified patent and that said Letters Patent is hereby corrected as shown below:

On Title Page:
Page 2, Other Publications, line 52: Please correct "Maňas et al." to read -- Mañas et al. --

Specification:
Column 3, Line 53: Please correct "off20%," to read -- of ± 20%, --

Signed and Sealed this
Twelfth Day of July, 2016

Michelle K. Lee
*Director of the United States Patent and Trademark Office*